United States Patent [19]

Kühl

[11] 4,236,502

[45] Dec. 2, 1980

[54] PORTABLE HEATING SYSTEM

[76] Inventor: Hans Kühl, Kornbergweg 12, D-7310 Plochingen, Fed. Rep. of Germany

[21] Appl. No.: 806,853

[22] Filed: Jun. 15, 1977

[30] Foreign Application Priority Data

Jun. 16, 1976 [DE] Fed. Rep. of Germany ....... 2626947

[51] Int. Cl.² .............................................. A61F 7/06
[52] U.S. Cl. ................................... 126/208; 126/204; 126/210
[58] Field of Search ...................... 126/208, 210, 204; 165/46; 48/174, 175, 176; 220/3

[56] References Cited

U.S. PATENT DOCUMENTS

| 464,872 | 12/1891 | Hollender | 126/210 X |
|---|---|---|---|
| 546,436 | 9/1895 | Springsteen | 126/210 |
| 554,121 | 2/1896 | Harmer | 126/208 |
| 675,089 | 5/1901 | Dolge | 126/210 |
| 687,004 | 11/1901 | Crawford | 126/210 |
| 1,121,277 | 12/1914 | Mitchell | 126/210 |
| 1,254,443 | 1/1918 | Spurr | 126/210 |
| 2,346,998 | 4/1944 | Reveno | 126/204 |
| 2,753,435 | 7/1956 | Jepson | 126/210 UX |
| 2,755,792 | 7/1956 | Van Hook | 126/210 |
| 3,034,495 | 5/1962 | Bernard | 126/210 |
| 3,110,301 | 11/1963 | Bricker | 126/208 |
| 3,406,678 | 10/1968 | Hanks | 126/208 |
| 3,572,314 | 3/1971 | Teague | 126/210 |
| 3,662,780 | 5/1972 | Marsh | 220/3 X |
| 3,875,924 | 4/1975 | Bayles | 126/204 |
| 3,892,225 | 7/1975 | Twose | 126/204 |

FOREIGN PATENT DOCUMENTS 1749 1/1878 Fed. Rep. of Germany .......... 126/210

Primary Examiner—Dennis L. Taylor
Attorney, Agent, or Firm—Craig and Antonelli

[57] ABSTRACT

A portable heating system for individuals which system includes a heating device for heating a quantity of fluid, an energy source for supplying a fuel to the heating device and an emitting device operatively connected with the heating device for emitting a quantity of heat. The energy source, the heating device and the heat emitting device are constructed as a structural unit with the heat emitting device being insertable into a sheath surrounding an individual so as to provide for the thermal requirements of the individual.

34 Claims, 6 Drawing Figures

PORTABLE HEATING SYSTEM

The present invention relates to a heating arrangement and, more particularly, to a portable heating system for individuals which includes an energy source or supply and a fluid heater connected with a heat emitting device.

A heating system is proposed in British Pat. No. 1,185,622 wherein a garment is provided with a system of conduits heated by hot water circulation. One disadvantage of this proposed heating system resides in the fact that, by virtue of the presence of the conduit system, the garment is relatively expensive to manufacture. Additionally, a further disadvantage resides in the fact that donning or removing the proposed garment, as would be the situation if the garment is used for hunting or military purposes, is cumbersome and the rapid management that is often necessary for these purposes is relatively difficult. Moreover, individual heat requirements of a particular user cannot be met because the conduit system is fixed to the garment.

The aim underlying the present invention essentially resides in providing a portable heating system which ensures, as to the amount of heat, the personal desires of the individual on various parts of the body can readily be obtained.

According to one feature of the present invention, an energy source or supply, a heating device and a heat emitting device are provided and fashioned as a single structural unit with the heat emitting device being insertable or introducible into a sheath surrounding the user.

According to a further advantageous feature of the present invention, the energy source includes a receptacle formed by a tubular member at respective end faces of which are provided inserts connected with the tubular member by soldering, welding, or the like.

Preferably, according to the present invention, the energy source or supply is provided with a conventional closure valve selectively connectable with an adapter for automatic filling of the energy source with an appropriate fuel. After the filling or recharging of the energy source or supply, the closure valve is then connected to a pressure regulator.

According to a further feature of the present invention, the heating device includes a burner connected at a lower end of a heating pipe, which heating pipe is enclosed by a jacket pipe or tube that contains a liquid to be heated by the heating pipe and circulated to the heat emitting device. The jacket or tube surrounds a pipe or tubular element having inserts at respective ends thereof joined to the pipe or tubular element by soldering, welding or the like, so as to define an annular chamber for accommodating the liquid to be heated between an outer surface of the heating pipe, an inner surface of the pipe or tubular element, and the respective inserts.

According to the present invention, the heat emitting device communicates with a forward running and reflux conduit arranged at respective inserts so as to communicate the heat emitting device with the annular chamber. To produce the appropriate gradient, the forward running conduit opens at the upper insert and the reflux conduit opens at the lower insert.

According to yet another feature of the present invention, a muffler is provided at a free end of the heating pipe and is formed by a plurality of tubular elements which fill up the entire cross-section of the heating pipe. Preferably, the muffler is arranged at the free end of the heating pipe with the free end being disposed at a right angle at least with respect to the upper portion of the heating pipe.

To maximize the efficiency of the heating unit and minimize heat loss therefrom, the outside of the jacket pipe is surrounded with an insulating layer of, for example, asbestos.

In accordance with a still further feature of the present invention, a convection device which extends essentially over the entire length of the jacket pipe is provided, which convection device, as viewed in cross-section, is formed of two trapezoidal elements, the shorter sides of which are combined along a longitudinal center plane of the heating pipe.

To ignite the burner of the heating device of the present invention, a match or lighter may be employed and, for this purpose, an opening is provided in the heating pipe in proximity to a tip of the burner. However, it is also possible in accordance with the present invention to ignite the burner of the heating device by a piezo-electric device.

Additionally, according to the present invention, an observation window may be provided in a housing accommodating the heating device so as to permit an observation of the operation of the burner and/or a photoconductive cable could be arranged in the housing to monitor the functioning of the burner.

According to the present invention, the heat emitting device is fashioned as a flexible hose assembly about six meters in length with the flexible hose assembly including end hose sections arranged immediately in the area of the heating device at the forward running conduit and the reflux conduit, with such hose sections being insulated. Preferably, the end hose sections are about two meters in length with a further intermediate hose section extending between the end hose sections being constructed in such a manner that a physiologically temperature is emitted by the heat emitting device.

According to a further feature of the present invention, the energy source and the heating device are disposed in a housing in parallel to one another with an appropriate inspection glass or window being provided in the housing to observe the functioning of the heating system.

Accordingly, it is an object of the present invention to provide a portable heating system which avoids by simple means the drawbacks and shortcomings encountered in the prior art.

A further object of the present invention resides in providing a portable heating system which is simple in construction and readily manageable.

Yet another object of the present invention resides in providing a portable heating system which is constructed as an air emersion device adapted to be inserted in a sheath surrounding the user of the heating system.

A still further object of the present invention resides in providing a portable heating system which does not require an expensive garment or complex heating conduit system.

Another object of the present invention resides in providing a portable heating system which can rapidly be put into operation and which ensures an adequate quantity of heat provided on the various parts of the user's body in accordance with the personal preferences and/or individual thermal requirements of the user.

A further object of the present invention resides in providing a portable heating system which permits the user to rapidly separate from the system even after a fairly long use which is of significance in hunting and millitary use of the heating system.

These and other objects, features and advantages of the present invention will become more apparent from the following description when taken in connection with the accompanying drawings which show, for the purposes of illustration only, several embodiments in accordance with the present invention, and wherein.

Figure 1:
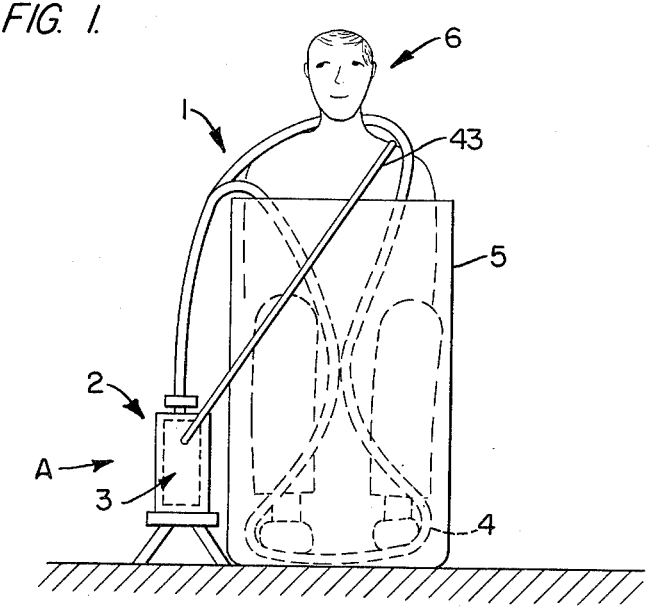
FIG. 1 is a partially schematic frontal view of a portable heating system in accordance with the present invention.

Referring now to the drawings wherein like reference numerals are used throughout the various views to designate like parts and, more particularly, to FIG. 1, according to this figure, a portable heating system generally designated by the reference numeral 1 is provided which includes an energy source or supply generally designated by the reference numeral 2 and a heating device 3 operatively connected with a heat emitting device 4 which is introducible or insertable into a sheath 5 which may, for example, be a sleeping bag, blanket, or the like, surrounding a person generally designated by the reference numeral 6.

Figure 2:
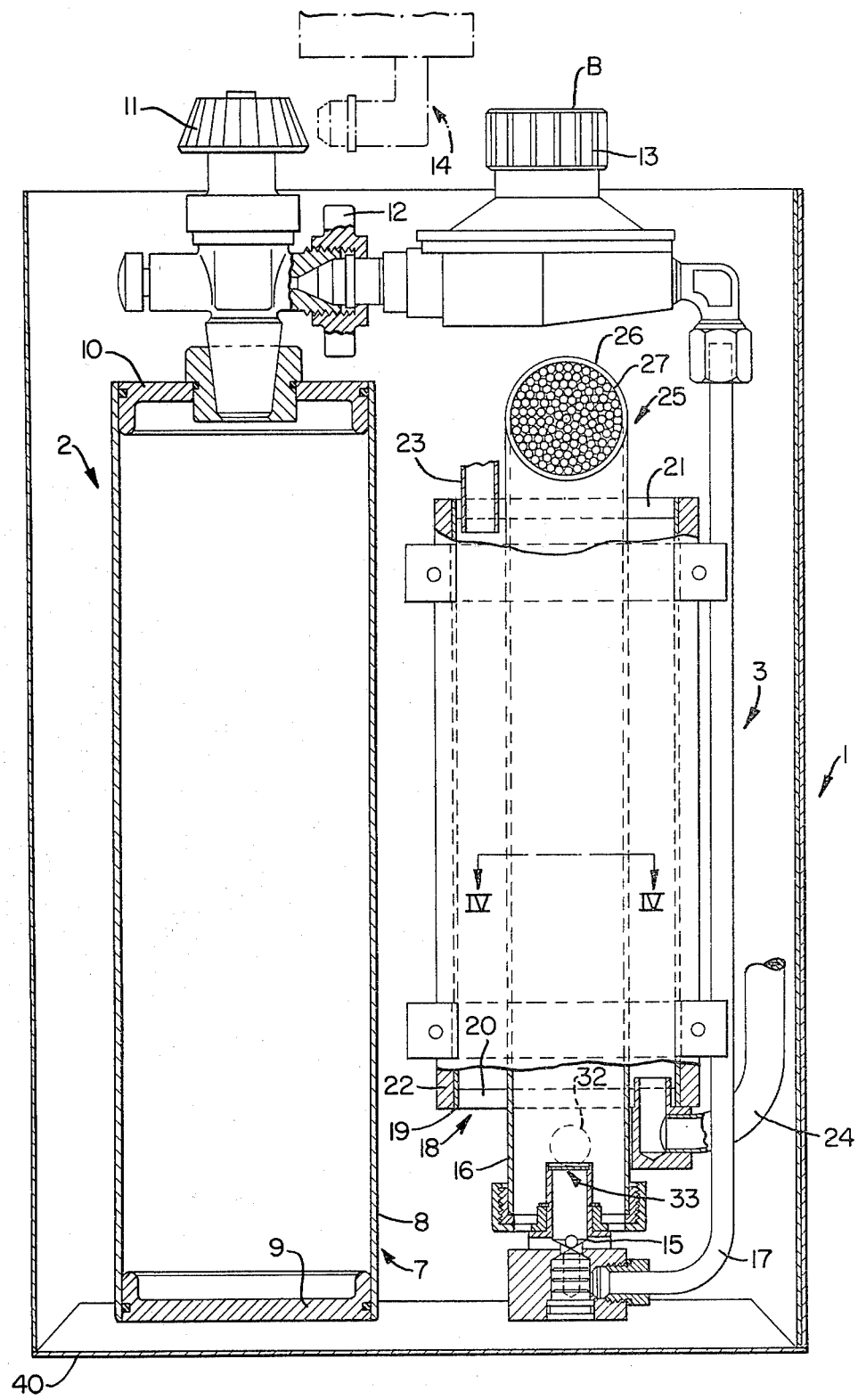
FIG. 2 is a partial cross-sectional view, on an enlarged scale, of the energy source and heating device in accordance with the present invention taken in the direction of the arrow A in FIG. 1.

As shown most clearly in FIG. 2, the energy source or supply 2 includes a receptacle generally designated by the reference numeral 7 having a pipe or tubular portion 8 at the respective end faces of which are provided inserts 9, 10 connected to the tubular or pipe portion 8 by soldering, welding, or the like. A valve closure 11 is provided at the upper end of the receptacle 7 and is connected by way of a wing nut 12 with a downstream pressure regulator 13. The closure valve 11 may also be connected with an adapter 14, indicated in dashed lines, so as to permit a re-filling or recharging of the receptacle 7 with a suitable energy supply such as, for example, propane gas or the like. The pressure regulator 13 is provided for adapting or controlling the gas pressure in accordance with varying external temperatures and, for this purpose, a scale (not shown) is disposed on a rotary part B of the pressure regulator 13. The heating device 3 is provided with a burner 15 connected to a heating pipe or tube 16 with a conduit 17 arranged between the burner 15 and the gas pressure regulator 13 so as to supply fuel from the energy source or supply through the valve 11 and pressure regulator 13 to the burner 15. A jacket pipe or tube generally designated by the reference numeral 18, filled with a fluid, surrounds the heating pipe 16 and also encloses a pipe or tube 19, the respective end faces of which have inserts 20, 21 connected with the pipe or tube 19 by soldering or welding.

An insulating layer 22 of, for example, asbestos, surrounds the outside of the jacket pipe 18 with a forward conduit 23 and a reflux conduit 24 of the heat emitting device 4 communicating with an annular chamber defined between the outer surface of the heating pipe 16, inner surface of the pipe 19, and inner surfaces of the inserts 20, 21. To avoid the necessity of a supplementary pump and to create an appropriate gradient, the forward conduit 23 opens at the upper insert 21 with the reflux conduit 24 opening at the lower insert 20. As readily apparent, the inserts 20, 21 are provided with appropriate openings or passages for permitting the heating pipe 16 to extend through the heating device 3 and also to permit the forward conduit 23 and reflux conduit 24 to communicate with the annular chamber in which is housed the liquid to be heated. So as to maintain the annular chamber fluid type, the openings accommodating the conduits 23, 24 and heating pipe 16 are connected with the inserts by, for example, soldering, welding, brazing, or the like.

A muffler 26 is provided at a free end generally designated by the reference numeral 25 of the heating pipe 16, which muffler is of particular importance in military or hunting use of the heating system 1. The muffler 26 includes a plurality of tubular elements 27 that fill up the cross-sectional area of the heating pipe 16 and, to obtain the most favorable flow of exhaust gas from the heating pipe 26, free end 25, in which the muffler 26 is disposed, is arranged at a right angle to the remaining portion of the heating pipe 16.

As also shown in FIG. 2, the energy source or supply 2 and the heating device 3 are disposed in parallel to each other in a housing 40 which the user may hang on his back like a knapsack as a single structural unit, thereby greatly facilitating the transportation and use of the heating system. For this purpose, a suitable strap 43 (FIG. 1) or the like may be provided and secured to the housing 40 in a conventional manner.

Figure 3:
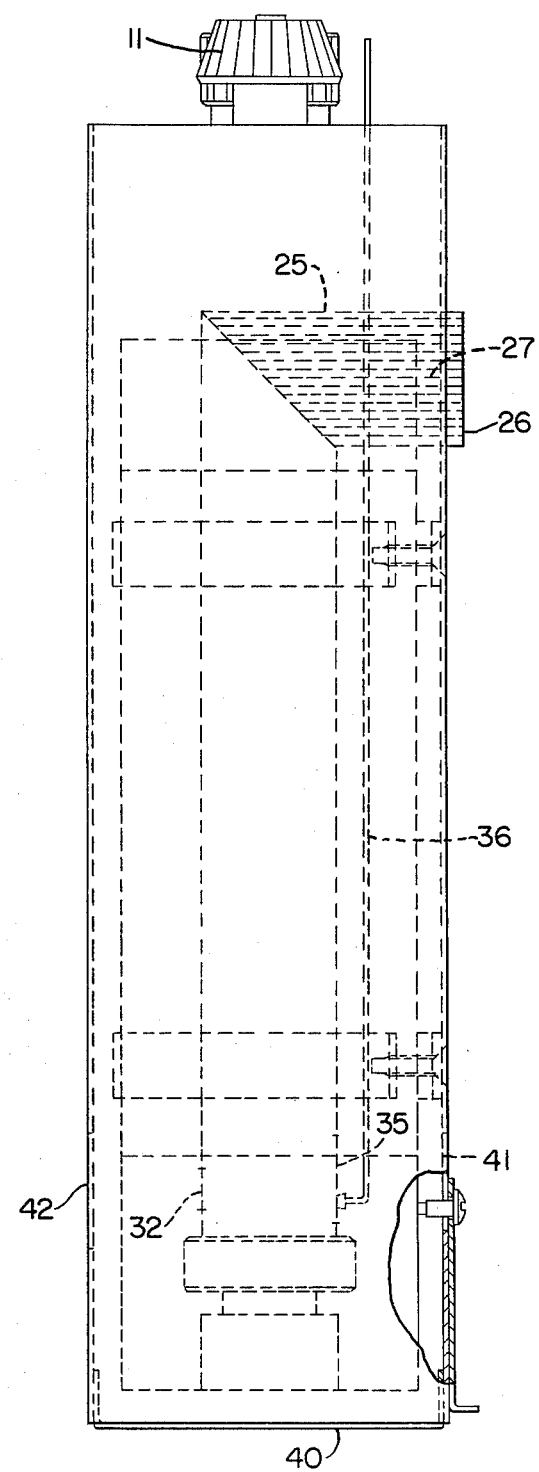
FIG. 3 is a lateral view of the portable heating system of FIG. 2.

As shown in FIGS. 2 and 3, an opening 32 is provided in the heating pipe 16 in close proximity to a burner tip generally designated by the reference numeral 33 of the burner 15, which opening 32 permits the introduction of a match or lighter into the heating pipe 16 so as to permit an ignition of the burner 15. To permit access to the opening 32, an opening 42 is provided in the housing 40 at a position opposite the opening 32.

To permit an observation of the functioning of the burner, as shown in FIG. 3, an observation window or glass 35 is provided in the heating pipe 16 with a further observation window or glass 41 being provided in the housing 40 at a position opposite the window 35. Moreover, in lieu of the observation windows 35, 41 or in addition to such windows, a photoconductive cable 36 may be arranged in the housing 40 at the heating tube 16 for monitoring the function of the burner 15.

Figure 4:
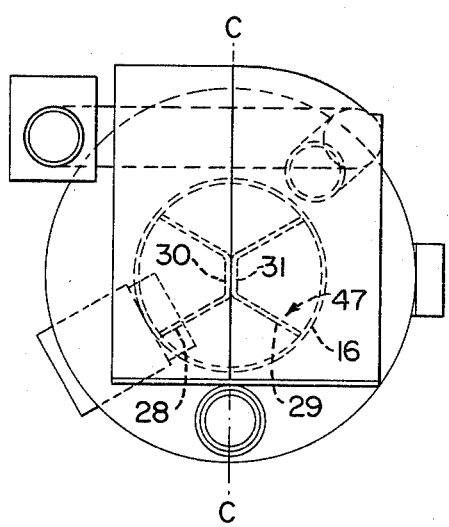
FIG. 4 is an enlarged sectional view taken along the line IV—IV of FIG. 2.
Figure 5:
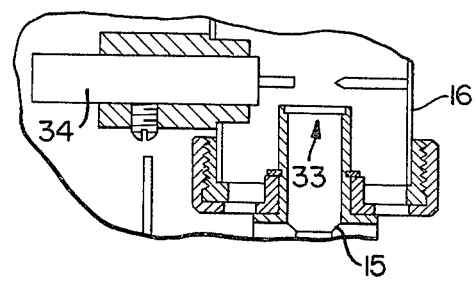
FIG. 5 is a partial cross-sectional view of a modified igniting arrangement in accordance with the present invention.

To enhance the efficiency of the heating device 3, as shown most clearly in FIG. 4, a convection device generally designated by the reference numeral 47 is arranged inside the heating pipe 16 and extends essentially over the entire length of the heating pipe 16. The convection device 47 is formed by two trapezoidal elements 28, 29 with the shorter sides 30, 31 of the respective trapezoidal elements 28, 29 being combined or joined along a longitudinal center plane C-C of the heating pipe 16.

Figure 6:
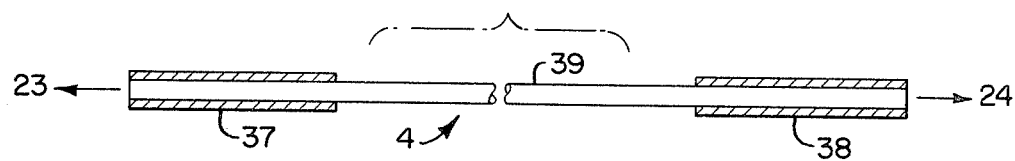
FIG. 6 is a partial cross-sectional view of a heat emitting device in accordance with the present invention.

The heat emitting device 4 includes a flexible hose about six meters in length which can be guided along the user's body in accordance with the user's personal thermal requirements. As shown in FIG. 6, the flexible hose includes end hose sections 37, 38 and an intermediate hose section 39. The hose sections 37, 38 are connected with the conduit 23 and reflux conduit 24, respectively, and provide an insulation in the area of the heating device with the intermediate hose section 39 being so designed that physiological temperatures of 40° C.-50° C. are emitted.

In operation, the valve 11 is first opened and pressure regulator 13 is set to an existing or anticipated outer temperature. Thereafter, burner 15 is ignited by matches or the like being introduced to the tip 33 of the burner 15 or by actuation of the piezo-electric device 34. After a given interval following ignition, liquid circulation begins from the annular chamber of the heating device 3 with the heated liquid passing through the forward conduit 23, end hose section 37, intermediate hose section 39, and reflux conduit 24 back to the annular chamber. Upon the circulation of the liquid, the individual 6 places the flexible hoses of the heat emitting device 4 in a desired position, for example, in the position shown in FIG. 1, and surrounds himself with the sheath 5. Upon the supply of fuel in the energy source or supply 2, the wing nut 12 is removed so as to permit removal of the pressure regulator 13 and insertion of the adapter 14, whereby the energy source or supply 2 is recharged.

While I have shown and described several embodiments in accordance with the present invention, it is understood that the same is not limited thereto, but is susceptible of numerous changes and modifications as known to those skilled in the art, and I therefor do not wish to be limited to the details shown and described herein, but intend to cover all such changes and modifications as are encompassed by the scope of the appended claims.

I claim:

1. A portable heating system for individuals, which system includes a means for heating a quantity of fluid, an energy source means for supplying a fuel to said heating means, and means operatively connected with said heating means for emitting a quantity of heat, characterized in that the energy source means, the heating means and the heat emitting means are constructed as a structural unit, a portable housing means is provided for accommodating both the energy source means and the heating means, the heating emitting means are insertable into a sheath surrounding an individual so as to provide for thermal requirements of the individual, and in that the heating emitting means is formed essentially of a flexible hose through which the fluid circulates, the flexible hose being connected to the heating means and forming a hermetically sealed system therewith so that a flow gradient is created whereby the fluid flows through the heating system without the provision of a fluid pump.

2. A portable heating system according to claim 1, characterized in the portable housing means in that the heating means and the energy source means are mounted in parallel relationship to each other.

3. A portable heating system according to claim 1, characterized in that the energy source means includes a pipe-shaped member having an upper end and a lower end, and in that insert means are secured at said upper and lower ends so as to close said pipe-shaped member and define with said pipe-shaped member a receptacle for accommodating a supply of fuel for the heating system.

4. A portable heating system according to claim 3, characterized in that said insert means are secured to said pipe-shaped member by one of soldering and welding.

5. A portable heating system according to claim 4, characterized in that the heating means and the energy source means are mounted in parallel relationship to each other.

6. A portable heating system according to claim 1, characterized in that the energy source means includes a valve means for selectively communicating the energy source means with the heating means, and in that said valve means includes means for accommodating an automatic filling adapter means for re-filling the energy source means.

7. A portable heating system according to claim 6, characterized in that a pressure regulator means is provided and connected downstream of said valve means, as viewed in a flow direction from the energy source means to the heating means.

8. A portable heating system according to claim 7, characterized in that the heating means and the energy source means are mounted in the portable housing means in parallel relationship to each other.

9. A portable heating system according to claim 1, characterized in that the heating means includes a heating pipe and a burner means operatively connected thereto.

10. A portable heating system according to claim 9, characterized in that a jacket means is provided and surrounds said heating pipe, said jacket means and said heating pipe defining an annular chamber means for accommodating the fluid to be heated.

11. A portable heating system according to claim 10, characterized in that said jacket means includes a pipe-shaped member having an upper open end and a lower open end, and in that insert means are secured at said upper and lower ends so as to close said pipe-shaped member, said annular chamber means being defined between an outer surface of said heating pipe, an inner surface of said pipe-shaped member, and inner surfaces of the respective insert means.

12. A portable heating system according to claim 11, characterized in that said insert means are secured to said pipe-shaped member by one of soldering and welding.

13. A portable heating system according to claim 11, characterized in that the heat emitting means includes a forward running conduit means arranged at one of said insert means and a reflux conduit means arranged at the other of said insert means with each of said conduit means communicating with said annular chamber means and said flexible hose being disposed between said conduit means.

14. A portable heating system according to claim 13, characterized in that the forward running conduit means is arranged at the insert means secured at the upper end of said pipe-shaped member and the reflux conduit means is arranged at the insert means secured at the lower end of said pipe-shaped member so as to produce the flow gradient for heated fluid.

15. A portable heating system according to claim 10, characterized in that insulating means are disposed about a periphery of said jacket means.

16. A portable heating system according to claim 15, characterized in that said insulating means is a layer of asbestos material.

17. A portable heating system according to claim 15, characterized in that the heating means and the energy source means are mounted in the portable housing means in parallel relationship to each other.

18. A portable heating system according to claim 9, characterized in that the heating pipe includes an upper and lower end, and in that said burner means is arranged at a lower end of the heating pipe.

19. A portable heating system according to claim 9, characterized in that an opening means is provided in the heating pipe to permit access to the burner for igniting the same by an igniting means.

20. A portable heating system according to claim 9, characterized in that a piezo-electric ignition means is arranged at said burner means for igniting the same.

21. A portable heating system according to claim 9, characterized in that a window means is arranged in the heating pipe in an area of said burner means for permitting observation of a functioning of said burner means.

22. A portable heating system according to claim 1, characterized in that said flexible hose has a length of about six meters.

23. A portable heating system according to claim 22, characterized in that said heat emitting means further includes a forward running conduit means and a reflux conduit means arranged at the heating means, and in that said flexible hose includes a pair of end hose sections and an intermediate hose section arranged between the end hose sections, said end hose sections being respectively connected with said forward running conduit means and said reflux conduit means and being insulated at least within an area of the respective conduit means.

24. A portable heating system according to claim 23, characterized in that said end hose sections are approximately two meters in length.

25. A portable heating system according to claim 24, characterized in that said intermediate hose section is constructed so as to emit a predetermined physiological temperature range.

26. A portable heating system according to claim 25, characterized in that said predetermined physiological temperature range is between 40° C.–50° C.

27. A portable heating system according to claim 26, characterized in that the heating means and the energy source means are mounted in the portable housing means in parallel relationship to each other.

28. A portable heating system according to claim 27, characterized in that a window means is arranged at the heating means for permitting observation of a functioning of the heating means, and in that a further window means is arranged in the housing means at a position opposite said first-mentioned window means.

29. A portable heating system according to claim 9, characterized in that the energy source means includes a pipe-shaped member having an upper open end and a lower open end, and in that insert means are secured at said upper and lower ends so as to close said pipe-shaped member and define with said pipe-shaped member a receptacle for accommodating a supply of fuel for the heating system.

30. A portable heating system according to claim 29, characterized in that the heat emitting means further includes a forward running conduit means and a reflux conduit means arranged at the heating pipe and communicating with said annular chamber means, and in that said flexible hose is arranged between said forward running conduit means and said reflux conduit means.

31. A portable heating system according to claim 30, characterized in that the heating pipe includes a free end portion, and in that a muffler means is arranged at the free end portion.

32. A portable heating system according to claim 31, characterized in that said flexible hose includes a pair of end hose sections and an intermediate hose section arranged between the end hose sections, said end hose sections being respectively connected with said forward running conduit means and said reflux conduit means and being insulated at least within an area of the respective conduit means.

33. A portable heating system according to claim 32, characterized in that convection means are provided and disposed within the heating pipe, said convection means extending essentially over the entire length of said heating pipe.

34. A portable heating system according to claim 33, characterized in that the heating means and the energy source means are mounted in the portable housing means in parallel relationship to each other.

* * * * *